US008834458B2

(12) United States Patent
Neuberger et al.

(10) Patent No.: US 8,834,458 B2
(45) Date of Patent: Sep. 16, 2014

(54) UROLOGICAL DIODE LASER SYSTEMS HAVING A GLASS-FIBER APPLICATION SYSTEM

(75) Inventors: Wolfgang Neuberger, Dubai (AE); Stefan Spaniol, Bonn (DE); Thomas Sandrock, Bonn (DE); Endrik Groenhoff, Bonn (DE)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 565 days.

(21) Appl. No.: 12/664,850

(22) PCT Filed: Jun. 16, 2008

(86) PCT No.: PCT/EP2008/004826
§ 371 (c)(1),
(2), (4) Date: Dec. 15, 2009

(87) PCT Pub. No.: WO2008/151840
PCT Pub. Date: Dec. 18, 2008

(65) Prior Publication Data
US 2010/0179523 A1      Jul. 15, 2010

(30) Foreign Application Priority Data

Jun. 15, 2007   (DE) .................... 20 2007 008 378 U

(51) Int. Cl.
*A61B 18/18*       (2006.01)
*A61B 18/24*       (2006.01)
*A61B 17/00*       (2006.01)
*A61B 18/00*       (2006.01)

(52) U.S. Cl.
CPC ....... *A61B 18/24* (2013.01); *A61B 2017/00274* (2013.01); *A61B 2018/00547* (2013.01)
USPC .......................................... 606/15

(58) Field of Classification Search
USPC ........................ 606/16, 14; 372/6; 29/426.2
See application file for complete search history.

(56) References Cited

U.S. PATENT DOCUMENTS

| 4,630,273 | A | * | 12/1986 | Inoue et al. | 372/9 |
| 2003/0179344 | A1 | * | 9/2003 | Van de Velde | 351/200 |
| 2006/0285798 | A1 | * | 12/2006 | Brekke et al. | 385/47 |
| 2007/0106286 | A1 | * | 5/2007 | Harschack et al. | 606/17 |

* cited by examiner

*Primary Examiner* — Tuan Nguyen
(74) *Attorney, Agent, or Firm* — Bolesh J. Skutnik; B J Associates

(57) ABSTRACT

The invention relates to a system for medicinal treatment, in particular for treating benign prostatic hyperplasia BPH, for use in the event of tumor resection or for use in thoracic surgery. The system comprises a diode laser device for producing a laser beam and to an application system based on optical wave guides that can be endoscopically introduced into a patient. Said system is designed in such a manner that the laser beam, produced by the diode laser device is guided through the application system and is emitted by said application system so that biological tissue can be treated in a selective manner with the emerging laser beam.

14 Claims, 2 Drawing Sheets time-dependent laser emission of a laser operating in "mixed mode" regime

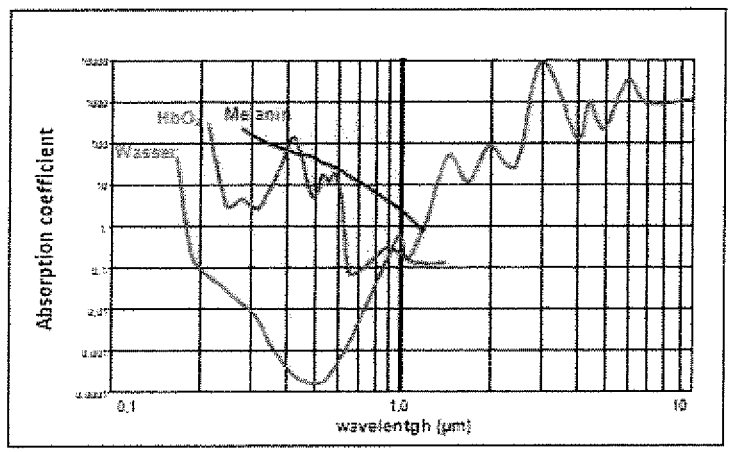
Fig. 1: Absorption by cells and tissue depending on the wavelength
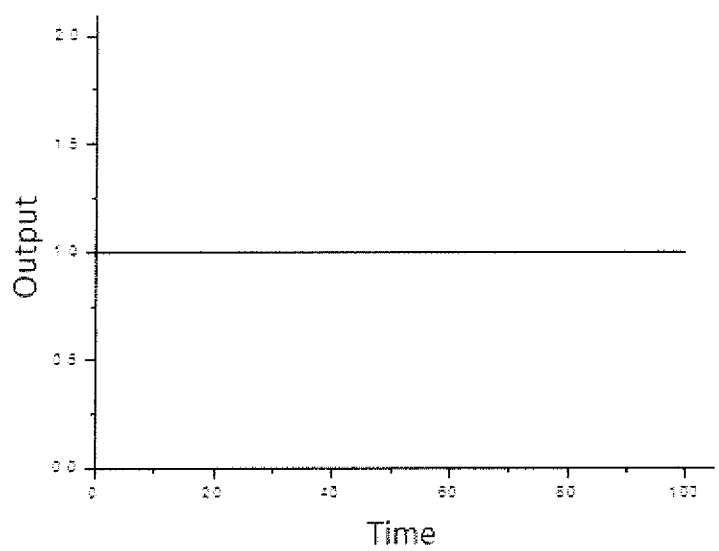
Fig. 2: time-dependent optical power of a cw laser

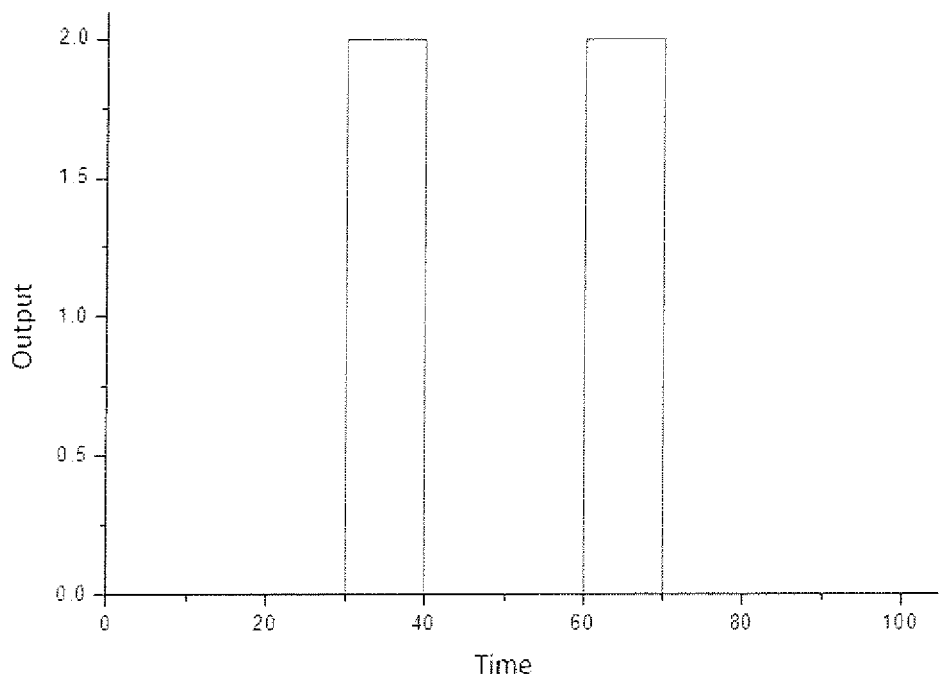
Fig. 3: time-dependent optical output of a pulsed laser system
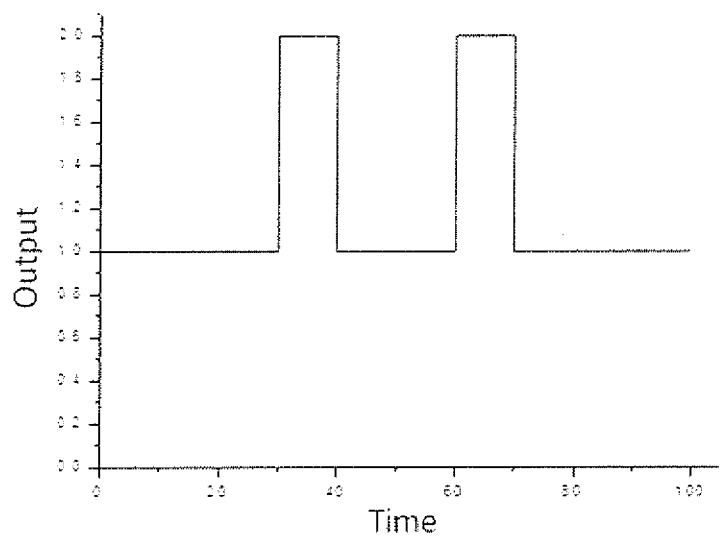
Fig. 4: time-dependent laser emission of a laser operating in "mixed mode" regime

UROLOGICAL DIODE LASER SYSTEMS HAVING A GLASS-FIBER APPLICATION SYSTEM

This applications claims the benefit of German application 20 2007 008 378.5 filed by the present inventors on 15 Jun. 2007 and International application PCT/EP2008/004826 filed by the present inventors on 16 Jun., 2008, both of which are incorporated by reference herein.

FIELD OF TECHNOLOGY

The present invention relates to the field of the medical treatment using laser energy. It relates further to the generation of appropriate laser radiation and its transmission over an optical fiber as well as to the therapeutic utilization of the laser radiation transmitted over optical fibers for selective treatment of urological tissues. The present invention is particularly useful for the medical treatment of the enlarged prostate (benign prostate hyperplasia, BPH) with selective endoscopic vaporization.

BACKGROUND

Benign prostatic hyperplasia (BPH) or "enlarged prostate" refers to the non-cancerous (benign) growth of the prostate gland. While BPH is the most common prostate problem in men over 50 years of age, the growth of the prostate begins with microscopic nodules around 25 years of age but rarely produces symptoms before the age of 40. It is estimated that 6.3 million men in the United States alone suffer from BPH. The disease is responsible for 6.4 million doctor visits and more than 400,000 hospitalizations per year.

The exact cause of BPH is unknown but it is generally thought to involve hormonal changes associated with the aging process. Testosterone likely plays a role in BPH as it is continually produced throughout a man's lifetime and is a precursor to dihydrotestosterone (DHT) which induces rapid growth of the prostate gland during puberty and early adulthood. When fully developed, the prostate gland is approximately the size of a walnut and remains at this size until a man reaches his mid-forties. At this point the prostate begins a second period of growth which for many men often leads to BPH later in life.

In contrast to the overall enlargement of the gland during early adulthood, benign prostate growth occurs only in the central area of the gland called the transition zone, which wraps around the urethra. As this area of the prostate grows, the gland presses against the urethra and causes a number of lower urinary tract symptoms (LUTS) such as difficult urination (obstructive symptoms) and painful urination (storage symptoms). Eventually, the bladder itself weakens and loses the ability to empty itself.

Obstructive symptoms such as intermittent flow or hesitancy before urinating can severely reduce the volume of urine being eliminated from the body. If left untreated, acute urine retention can lead to other serious complications such as bladder stones, urinary tract infections, incontinence, and, in rare cases, bladder damage and/or kidney damage. These complications are more prevalent in older men who are also taking anti-arrhythmic drugs or anti-hypertensive (non-diuretic) medications. In addition to the physical problems associated with BPH, many men also experience anxiety and a reduced quality of life.

Initial symptoms of BPH are most often treated with medication such as alpha-blockers and anti-androgens. Men suffering with moderate to severe BPH symptoms typically must undergo surgery. Transurethral resection of the prostate (TURP) is the standard surgical procedure, which however may lead to a number of complications:

Bleeding or secondary hemorrhage
    The shallow penetration of the tissue in combination with the resection of large volumes leads to an opening of many vessels, which subsequently bleed into the cavity of the surgery. In approximately 1% of cases this leads to severe hemorrhages. with the result that even a blood transfusion may be required. Sometimes, due to a secondary hemorrhage, a surgical hemostasis with another narcosis may become necessary. In all cases continuous flushing is required to ensure free visibility. Moreover, patients remain in hospital under postoperative supervision for 5-7 days to enable an adequate response in cases of secondary hemorrhages. Even coughing can cause such hemorrhages.

"TURP-syndrome"
    Within the resectoscope there is a wire loop fed by an electric current. This wire removes layers of diseased tissue in the bladder or prostate while hemorrhages are cauterized through electricity. The physical principle corresponds to the one employed in RF-surgery. Throughout the operation, irrigation liquid is continuously introduced via the resectoscope, serving the filling of the bladder on one hand and the excretion of resected tissue and blood on the other. This solution is hypotensive, i.e. it has a lower concentration of electrolytes than the blood. The low electrolyte concentration is necessary to ensure a low conductivity. Through the flushing of water into open blood vessels the salt and water balance can be disturbed ("infiltration"). The result is cardiac and circulatory stress, which may lead to acute right-sided heart failure. These may even end fatally. Symptoms are nausea, vomiting, confusion and restlessness.

Incontinence, i.e. the inability to retain urine deliberately.
    The frequency can vary greatly. The complication is rare with an experienced surgeon (approx. 1%). On the other hand an incontinence caused by BPH can improve after the operation.

Impotence
    Here the incidents also vary considerably (10-15%). One possible cause is the damage to nerves at the outer side of the prostate capsule through electricity; psychological factors are also being discussed. Overall only a small number of patients are affected. Studies regarding impotence and BPH indicate that impotence occurred with a variety of treatments (including waiting).

Cystitis and epididymitis occur frequently but respond well to antibiotic treatment.

Discharge of seminal fluid into the bladder (60-80%).

Perforation of prostate capsule or rectum.

Potential long-term consequences are:

Erectile dysfunction.

Retrograde ejaculation (no emission of semen).

Months or years after the treatment a stricture of the urethra through scarring as well as a narrowing of the bladder neck may occur. A renewed formation of adenoma is also possible.

However, a number of other, less invasive methods are nowadays available:

transurethral incision of the prostate (TUIP), transurethral microwave thermotherapy (TUMT), transurethral electro vaporization (TUVP), transurethral needle ablation (TUNA), and laser surgery of the prostate gland.

In the TUMT, the target tissue is heated through a microwave probe. Since only sedation is required, this treatment suggests itself in cases where the narcosis would present a high risk for the patient. The treatment is however only possible where the prostate has a small volume. Contraindications for the TUMT are pacemakers or metals in osteosynthetic materials.

A TUNA is also performed under local anesthesia, which means that the treatment can also be applied in high risk patients. However, it is only appropriate tfor a prostate volume of <60 ml. There are no reliable data at present about the effectiveness of the treatment. In up to 14% of cases a renewed operation is required.

In the adenoma enucleation (removal of prostate tissue through surgical incision) large volumes of prostate tissue of more than 75 ml can be removed. An indication for this operation can also be a symptomatic diverticulum of the bladder (outwards protuberance of the bladder wall) or a large bladder stone. It is an advantage that the outlet of the bladder is in direct visibility for the surgeon, so that injuries to the bladder can certainly be avoided. The adenoma can be removed completely. The complications of a TURP-syndrome do not occur. As with all 'open operations' this procedure however requires longer hospitalization.

Nowadays the above mentioned urological indications can be treated alternatively by means of laser radiation. In comparison with the "classical" forms of treatment these procedures have the advantage of superior hemostasis (arrest of bleeding) and minimal invasive surgery.

Various systems are currently employed for the therapy with laser radiation through solid-state lasers, such as diode-pumped solid-state lasers (DPSSL) or frequency doubled DPSSL. In these treatments light is generated through flashlights or laser diodes, which in turn is used for the stimulation of the solid-state laser. A few examples of such systems and the applied solid-state lasers are described in the following.

The so-called KTP laser (potassium-titanyl-phosphate laser), which is a frequency doubled solid-state laser with a wavelength of 532 nm, has primarily an ablative effect, which means that the target tissue is vaporized. Typical laser parameters are pulse durations of a few micro- to milliseconds as well as applications in continuous (continuous wave, cw) with a medium power of about 80 W. An advantage of this form of therapy is that the patient requires a bladder catheter only briefly, i.e. for 1 to 2 days. Disadvantages are the high costs for laser and application system based on glass fiber. Moreover, there is a danger of perforation of the bladder wall, with potential lethal consequences if the glass fibers should break.

The Nd:YAG-Laser (neodymium-doped yttrium aluminum garnet laser) emits light with a wavelength of 1064 nm, having a secondary ablative (coagulating) effect, and causing necrosis in the tissue, which desquamates within four weeks. During this time the patient has to tolerate a bladder catheter, i.e. the healing process is prolonged and the patient does not experience an immediate alleviation of his ailments. Typical parameters of treatment are pulse durations of a few micro- to a few milliseconds and cw-applications with a medium power of about 80 W.

Interstitial laser coagulation, in other words, coagulation within the tissue leads to a reduction of the adenoma volume through atrophy and scarring. Since no tissue is removed there is no immediate alleviation. The treatment is minimal invasive but causes higher costs.

All these systems have one disadvantage in common, which is the fact that they principally require a light source in addition to the solid-state laser, yielding to a relatively inefficient conversion of electric power to optical power ("wall plug efficiency"). The described lasers are mostly equipped with a three-phase connection and frequently need water cooling. Even up-to-date systems, operating on one phase only, require a fuse protection of up to 32 A. This requires special installations for a corresponding electrical power supply to operate these systems, which prevents the mobile application of these systems. The heaviness of such systems, weighing about 140 kg or more, in addition to the requirements of a cooling medium, makes a mobile application prohibitive, too.

Furthermore, the complex configuration of such systems, especially the use of consumables such as flash lamps or of cooling systems with liquid cooling agents, requires regular and sometimes costly maintenance, which is also a disadvantage.

SUMMARY

It is therefore an objective of the present invention to provide a system for medical treatments, especially for the treatment of BPH, which allows a mobile application.

It is another objective of the present invention to provide a system for medical treatments, especially for the treatment of BPH. which requires little maintenance.

It is yet another objective of the present invention to provide a system for a given medical treatment, especially the treatment of BPH, which is suitable for the best possible treatment while minimizing potential side effects and hemorrhages, especially through appropriate choice of wavelength, power density, and/or pulse duration respectively cw-operation.

Furthermore, today's laser devices emit optical power either continuously (cw) or in the form of laser pulses. In order to ablate of vaporize efficiently tissue in the cw mode, a relatively high power $P_{cw}$ is necessary. This can be so high that it results in undesirable large coagulation seams or even formation of necrosis due to photo-thermal effects and long exposition times. In case, tissue shall be removed in an ablative or vaporizing way, pulsed mode (with pulse durations in the range from microseconds to milliseconds) of laser emission is often used. At this, only small coagulation seams are often created so that bleeding-free operating or operating with only weak bleeding is not possible and the danger of perforation of tissue structures arises. Thus, it would be desirable to remove tissue without bleeding from the surrounding tissue areas and without any perforation of neighbored tissue structures. Besides the already mentioned urological treatment of BPH. there is a multitude of additional applications that would benefit from such a comparatively gentle treatment. These medical application are found e.g. in the field of general surgery, gynecology, urology and tumor therapy. Two further examples are tumor resection and thoracic surgery.

In a tumor resection procedure, some types of tumor tissue must be coagulated first, before they can be resected, in order to reduce the danger of a formation of metastases. So far, mainly diode lasers (e.g. 940 nm) and solid-state lasers (e.g. Nd:YAG, 1064 nm) have been used in gastroscopic, bronchioscopic or rectoscopic treatments. First, tumor tissues is coagulated a low laser power to be removed at high power afterwards. The danger of perforation of surrounding tissue structures exits due to the large penetration depth of laser radiation at wavelengths of 940 nm and 1064 nm, respectively. Possibly, a too low laser power is applied in order to avoid such a perforation and thus results in an insufficient coagulation.

In thoracic surgery, lung tissue is removed with a solid-state laser operating at a wavelength of 1320 nm during a partly resection of the lung. This laser is mainly effective in an ablative way. Alternatively, diode lasers (λ=980 nm) are used for a short time. These diode lasers feature significantly better coagulation properties. Optical powers of more than 80 W are required in order to efficiently remove tissue at this wavelength. Therefore, it is another objective of the invention to provide a system for medical treatments, especially for the treatment of BPH, which allows for removal of tissue without bleeding from surrounding tissue areas and without perforation of neighbored structures, respectively.

These and other objectives of the present invention are solved with a system under the terms of claim 1. Further preferred embodiments are described in the dependant claims.

The present invention permits particularly the supply of systems with a high effectiveness, exemplary exceeding 55%, which permits the cooling to be realized as forced air cooling and to do without the maintenance intensive, complex, and heavy water cooling systems. In this manner, systems with relatively little weight, e.g. below 40 kg, can be realized. The high effectiveness also allows such systems to be operated with a single phase electrical connection with 230V and 10 A. This has the advantage that such systems are transportable and can be put in use almost anywhere without any special electrical power supply and cooling systems.

Furthermore. such systems require very little maintenance because they do without easily deteriorating parts and consumables such as flash-lamps or water-cooling systems.

Through simple modular system concepts the necessary performance can be reached with simultaneous flexibility of all treatment parameters such as power, pulse duration (several microseconds to seconds), and pulse pause (several microseconds to seconds).

Such systems have the potential to perform BPH treatments up to the highest prostate volumes and weights of up to 200 grams. There is no contraindication known as yet, which means that for instance patients taking hemodilution medications or suffering with cardiac and circulatory disorders can also be treated.

Moreover, the present invention provides systems that allow for a combined irradiation with continuous laser emission and additional laser pulses. This is particularly advantageous in applications that require the tissue removal with only weak bleeding, especially the removal of larger volumes of tissue. The thermal input is reduced in comparison with conventional cw-laser systems and thus, a smaller area is coagulated. Together with the higher pulse peak power, tissue can be vaporized precisely, while a small coagulation seam, preventing or reducing bleeding, is generated at the same time.

BRIEF DESCRIPTION OF THE DRAWINGS

The above and other advantages, features and qualities of the present invention will become apparent from the following description, which is only exemplary and not descriptive, read in conjunction with the accompanying drawings, showing:

FIG. 1: Absorption by cells and tissue depending on the wavelength;

FIG. 2: time-dependent optical power of a cw laser;

FIG. 3: time-dependent optical output of a pulsed laser system; and

FIG. 4: time-dependent laser emission of a laser operating in "mixed mode" regime.

DETAILED DESCRIPTION

According to the present invention, a system for medical treatments is equipped with a diode laser device for the generation of laser radiation as well as with an application system based on an optical waveguide, which can be inserted endoscopically into the patient. The laser radiation produced by the diode laser device is transmitted through the application system and emitted by the application system, so that biological tissue can be treated selectively with the emitted laser radiation, e.g. through coagulation, vaporization or incision.

The diode laser device used in the system according to the invention is capable of converting electric current directly into laser light, which is usable for medical treatment. Therefore the need for additional flash-lamps or laser diodes to stimulate the laser, as they are used in previously known systems based on solid-state lasers, becomes superfluous, thus achieving a considerably simplified construction of the system. Additionally such diode lasers have a high effectiveness of partly over 55%. This allows dispensing with laborious cooling systems such as water-cooling.

Furthermore, such diode lasers are available at wavelengths within a spectral range between 800 and 2000 nm, enabling the supply of systems for medical treatment, through appropriate choice of wavelength and/or power density, which are "made to measure" so to speak for a given treatment, while at the same time offering high performance and a good life expectancy of over 3000 operating hours. Single laser diodes as well as laser diode bars can be used for diode laser devices.

The application system preferably features a urological instrument, for example a cysto-urethroscope. through which a suitable optical fiber is guided, which is connected to the light emitting (connecting) port of the diode laser system. Laser light is launched into the fiber core of the optical fiber, transmitted within the core to the distal end of the optical fiber and emitted from there.

The optical fiber is preferably equipped with two devices, which limit the possibility of moving it forwards and backwards within the urological instrument. Thus the optical fiber is prevented from being pushed too far out of the urological instrument, which reduces significantly the dangers of breaking the fiber or perforating the tissue through mechanical impact of the optical fiber. The limitation of backward movement provides inter alia protection for the endoscopic optics, which are integrated into the urological instrument, respectively protection of the instrument itself. Such an optical fiber preferably has the following values:

Fiber Parameters:
Diameter of the fiber core $\varnothing_{core} \geq 400$ µm
Numerical aperture NA=0.22
Fiber core made of silica
Jacket made of biocompatible material, e.g. Tefzel Alternatively, in a so-called "side-fiber" application system, a silica fiber can be used, where the output of the laser radiation is not via the fiber end face but via a small area of the cladding surface. This "side fiber" is connected with the light emitting output port of the diode laser. Laser light is launched into the fiber core, transmitted through the fiber core to the distal end of the optical fiber and emitted laterally through its cladding surface. The optical fiber is inserted within a urological instrument, e.g. a cysto-urethroscope. A corresponding optical fiber is for example shown in the document WO 2007/058891, to which is referred for further details about the design of such a "side fiber". Preferably this optical fiber also consists of the fiber parameters mentioned above.

In a first special embodiment of the present invention a diode laser system with a wavelength of 980 nm±30 nm with an average power above 100 W is applied. The laser radiation is launched into an optical fiber with a core diameter of 400 µm or more.

An advantage of the application of a wavelength of 980 nm is that due to the equally good absorption in water and blood an ablation is achieved, which is comparable with the ablation qualities of the KTP-laser. The tissue is removed superficially, and additionally coagulated to a depth of several millimeters, so that the arterial or venous vessels there are closed. Thus the incidence of hemorrhages is almost eliminated. This is considered a great advantage, since the requirement of a blood transfusion, as it may be necessary in a TURP, even nowadays has to be regarded as risky. A reduction of intra- and postoperative blood loss remains to represent one of the most important aspects of the surgical treatment of BPH.

Through the large variety of available medical fibers and application systems based on optical waveguides, applications are also possible in the upper urinary tract (pole amputation).

The effectiveness of this first special embodiment has been confirmed in first trials. It has been demonstrated, that the power can be reduced to about 60 W; however, this will be at the expense of the speed of procedure and possibly the result of the treatment. Below the set of parameters applied in the trials is listed:

Set of Parameters for Treatment
Pulse duration (time interval during which laser radiation is emitted):
10 ms or 100 ms or 200 ms or 1000 ms
Pulse pause (time interval between two laser pulses):
10 ms
Average laser power:
100-250 W
Fiber parameters
See above.

In a second special embodiment the first special embodiment is modified in such a way that now a diode laser with an emission wavelength of 940 nm+30 nm is used, the laser radiation of which is launched into an optical fiber with a core diameter of 400 µm or more.

Set of Parameters for Treatment
Pulse duration (time interval during which laser radiation is emitted):
10 ms or 100 ms or 200 ms or 1000 ms
Pulse pause (time interval between two laser pulses):
10 ms
Average laser power:
100-250 W
Fiber parameters
See above.

In a third special embodiment the first special embodiment is modified in such a way that a diode laser with an emission wavelength of 810 nm±30 nm is used, the laser radiation of which is launched into an optical fiber with a core diameter of 400 µm or more.

Set of Parameters for Treatment
Pulse duration (time interval during which laser radiation is emitted):
10 ms or 100 ms or 200 ms or 1000 ms
Pulse pause (time interval between two laser pulses):
10 ms
Average laser power:
≤100 W
Fiber parameters
See above.

In a fourth special embodiment the first special embodiment is modified in such a way that now a diode laser with an emission wavelength of 1470 nm is used. The choice of this emission wavelength has shown in trials to be particularly interesting, because at this wavelength the depth of penetration in water is much reduced due to the absorption coefficient, which is 30 times increased in comparison with the wavelength $\lambda$=980 nm.

This absorption behavior and also the penetration depth of main constituents of tissues water $H_2O$, hemoglobin $HbO_2$, and melanin, all dependent on wavelength, are shown in FIG. 1, considering that in the case of urology mainly the two first mentioned substances are relevant. In FIG. 1 the vertical scale with the values $\alpha(cm^{-1})$ represents the absorption coefficient for water respectively melanin. The scale $\epsilon(mM^{-1}cm^{-1})$ represents the concentration dependent absorption coefficient for hemoglobin ($HbO_2$) in the unit per milliMoles per cm. The penetration depth is the reciprocal value of the absorption coefficient. A lesser penetration depth means that the laser radiation is already absorbed earlier and does not penetrate as deeply into the tissue, which consists, as generally known, in large part of water. Accordingly only a smaller volume of tissue is being treated. A lesser penetration depth therefore permits the surgeon to work with higher precision, thereby reducing the area of collateral damage.

First trials with prostates of dogs have been conducted in order to test the effect of 1470 nm in diode laser technology. Here average power of approx. 40 W turned out to be sufficient for a selective vaporization of tissues.

Set of Parameters for Treatment
Pulse duration (time interval during which laser radiation is emitted):
100 ms
Pulse pause (time interval between two laser pulses):
10 ms
Average laser power:
40 W
Fiber parameters
See above.

In a further special embodiment a diode laser with a wavelength of $\lambda$=1.95 µm=1950 nm is applied. Here passively cooled laser diode bars with an output power of about 10 W are currently available. Systems for urological applications which achieve an average power of approximately 50 W are constructed in a modular way.

Laser radiation with this wavelength has a lesser coagulating effect, however the incisor effect is precise. Through the high absorption of water in this spectral range, water is however heated by the absorbed laser radiation to such a degree that vapor bubbles may occur, which in turn can lead to tissue coagulation.

Currently lamp-respectively diode-pumped thulium- and holmium-doped solid-state lasers are being applied. Urological thulium-doped solid-state lasers emit at a wavelength of 2040 nm. The absorption coefficient is here about 2.5 times higher than with a wavelength of $\lambda$=2140 nm as generated by holmium-doped solid-state lasers.

In comparison, diode lasers emitting at 1950 nm, benefit from a 1.5 times better absorption in comparison with the thulium-laser wavelength, as well as from the fact that with increasing tissue temperatures the maximum of water absorption moves towards shorter wavelengths. Therefore it is expected that in comparison with the emission of thulium- and holmium-lasers an even better absorption of the diode laser radiation can be achieved.

Moreover, the diode laser that is used in the system according to the present invention can be operated in a so-called "mixed mode". Laser power is emitted as a combination of continuous power output together with laser pulses of feasible pulse duration in such a way that the resulting emitted laser power reveals time dependence as shown schematically in FIG. 4.

Preferably, the cw power $P_{cw}$ as well as the pulse peak power $P_{peak}$ are independently selectable in "mixed mode" operation. Preferably the ratio $P_{cw}/P_{peak}$ is independently selectable, too. It is particularly preferred that pulse duration $t_{pulse}$, pulse pause $t_{pause}$, which is defined as the time interval between the ending of one pulse and the beginning of the next pulse, as well as the number of pulses are adjustable.

The preferred pulse duration of such laser pulses that act in an ablative/vaporizing way is shorter than the time constant of the thermal conductivity of the target tissue. Typical pulse duration is in the range from 0.01 to 100 ms.

Preferred wavelengths of such a laser system are in the spectral region from 800 to 1000 nm. Particularly preferred are the wavelengths 810, 940 and 980 nm.

Another preferred spectral region ranges from 1400 to 1500 nm. A particularly preferred wavelength is 1470 nm.

Due to a combination of continuous laser emission in conjunction with laser pulses of appropriate pulse duration and pulse peak power, "mixed mode" operation allows for simultaneous efficient removal of tissue and the formation of a coagulation seam that prevents bleeding or reduces bleeding as far as possible. Ablation and coagulation properties can be influenced by the choice of laser parameters ($P_{cw}$, $P_{peak}$, $t_{pulse}$, $t_{pause}$). Laser pulses with the higher peak power ($P_{peak} > P_{cw}$) yield an ablation/vaporization of the tissue. Due to the pulse duration and the pulse pauses, unnecessary thermal loading of the target tissue and surrounding tissue areas is avoided. Such thermal loading can possibly yield undesired formation of necrosis. However, simultaneous continuous power output ($P_{cw}$) yields a coagulated area so that tissue can be removed by the laser pulses without any bleeding or with reduced bleeding.

Besides the already mentioned urological treatment of BPH, there is a multitude of additional applications that might benefit from the invention of "mixed mode" operation. Here, tissue shall be removed without bleeding from surrounding tissue areas and without perforation of neighbored structures, respectively. Those medical applications are found in the field of general surgery, gynecology, urology and tumor therapy. Two additional examples are thoracic surgery and tumor resection.

A combined irradiation with cw laser emission and additional laser pulses is advantageous in thoracic surgery, especially in a partly resection of the lung as larger tissue volumes can be removed with reduced bleeding. The reduced thermal input (due to a cw power that is reduced in comparison with conventional cw laser devices) yields coagulation of a smaller area. In conjunction with the higher pulse peak power, tissue can be vaporized precisely, while a small coagulation seam is simultaneously generated that prevents or reduces bleeding, respectively.

During a tumor resection procedure, a laser device that is capable of "mixed mode" operation allows for a new approach of treatment: First, coagulation of tumor tissue results from non-contact treatment, e.g. at a wavelength of 980 nm and at power levels from 50 to 80 W. The tissue that has been pretreated in such a way can be removed efficiently and safely by laser vaporization afterwards.

While systems with diode laser devices for the generating of laser radiation at a single wavelength are described in the preceding paragraphs, it is possible in another, specific embodiment to provide a system with an additional, second diode laser device so that the system generates laser light at two different wavelengths ($\lambda_1$, $\lambda_2$), which have different penetration depths in biological tissue.

Light from both radiation sources is combined (e.g. by collinear superposition) by optical means (e.g. a dichroic mirror) so that laser radiation of both wavelengths can be launched to a common application system. Light of both wavelengths is guided and transmitted by the application system to the same treatment site so that one and the same target tissue can be irradiated and thus treated by at least one of the two wavelengths or by both wavelengths simultaneously.

In this process, light at the first wavelength $\lambda_1$ can be used e.g. for coagulation of the tissue while radiation at the second wavelength $\lambda_2$ can be used for ablation/vaporization of the tissue and thus for precise cutting/incisions.

Coagulation seam, depth of the incision and their relation can be influenced and adjusted to the respective medical treatment by variation of the respective (cw-) powers $P_1$, $P_2$ and the ratio $P_1/P_2$. $P_1$ and $P_2$ can be adjusted independently from each other. Thereby, the power levels $P_1$ (according to the wavelength $\lambda_1$) and $P_2$ (according to the wavelength $\lambda_2$) and the temporal behavior can be adjusted in such a way that one laser source emits continuously optical power (cw mode) while the second radiation source is operated with pulsed output. For "mixed mode" operation, the combination of 980 nm- with 1470 nm-laser radiation is a preferred selection.

The power levels $P_1$ and $P_2$ can be adjusted as well in such a way that both laser sources emit continuously optical power (cw mode) or the power levels $P_1$ and $P_2$ can be adjusted so that both radiation sources are operated in pulsed mode. Alternatively, it is possible that one of the laser sources is operated in the "mixed mode" regime while the other laser sources is operated in cw mode or in pulsed mode.

It is preferred that wavelength $\lambda_1$ is selected from the spectral region from 800 nm to 1100 nm, while $\lambda_1$ is selected from the spectral region from 1400 nm to 1500 nm or from the spectral region from 1900 to 2000 nm. Particularly preferred is the combination of wavelength $\lambda_1=980$ nm and $\lambda_2=1470$ nm.

Whereas optical power levels of more than 100 W at a wavelength of 980 nm are used in urological treatments today, the power levels that are necessary for ablation/vaporization and coagulation can be dosed more accurately and the different light-tissue interaction characteristics of $\lambda_1$ and $\lambda_2$ can be exploited beneficially by the use of a system with two diode laser devices that emit light at two different wavelengths. A total power $P_1+P_2<100$ W is expected. Combining two laser wavelengths with an adequate adjustment of the powers $P_1$, $P_2$ and the ratio of both power levels allows for an medically beneficial effect in ablation (effective but precise removal of tissue, even of large volumes) and coagulation (bleeding-free treatment or at least treatment with reduced bleeding). This is advantageous to the patient in that the treatment can be performed more efficiently and thus faster while being simultaneously safer.

Coagulation by the first of the two wavelengths reduces the risk of a perforation of the wall of the bladder as it can occur in a treatment with lasers that act in a primary ablative way (e.g. KTP laser).

As the case may be, the use of an ablative wavelength reduces side effects (especially the danger of the formation of necrosis that prolong the healing process) that are observed when lasers are used that act solely in a secondary ablative way (e.g. Nd:YAG laser).

The user (physician) can apply the two wavelengths apart or simultaneously and thus, he can cut and coagulate without changing the laser system and/or the application system during the treatment. The latter is advantageous especially in applications inside the patient's body.

What is claimed is:

1. A medical treatment system comprising:
   a diode laser system for the generation of laser radiation; and
   an application system based on optical waveguide, which can be inserted endoscopically into the patient;
   wherein said laser radiation has a wavelength in the spectral range of 800-2000 nm;
   wherein said medical treatment system is constructed in a way that the laser radiation generated by the diode laser system is transmitted through the application system and emitted by the application system, so that biological tissue can be treated selectively with the emitted laser radiation;
   wherein said laser system emits light at a first wavelength $\lambda_1$ and wherein said laser system also emits a light at a second wavelength $\lambda_2$, which is different from the wavelength $\lambda_1$;
   wherein the wavelength $\lambda_1$ is selected within the spectral region from 800 to 1100 nm and where the wavelength $\lambda_2$ from the spectral region from 1400 to 1500 nm or from 1900 to 2000 nm;
   wherein said medical treatment system is configured to operate in a mixed mode where laser radiation is emitted by the application system as a combination of simultaneous continuous emission (cw) and pulsed emission;
   wherein said medical treatment system is configured to control a parameter of the continuous emission of the laser radiation separately from a parameter of the pulsed emission of the laser radiation.

2. The system according to claim 1 wherein said selective treatment of biological tissue is performed by coagulation, vaporization or incision.

3. The system according to claim 1 being able to transmit laser radiation via the application system onto the target tissue with a power density above 5 kW/cm² for wavelengths in the spectral range of 800-1100 nm, respectively with a power density above 3 kW/cm² for wavelengths in the spectral range of 1400-1500 nm.

4. The A system according to claim 1 wherein said diode laser device has an average laser power above 100 W at a wavelength in the spectral range of 800-1100 nm, while this power can be emitted in continuous wave mode or by several pulses at pulse durations of a few microseconds to a few seconds.

5. The system according to claim 1 wherein said diode laser device has an average laser power above 50 W at a wavelength in the spectral range of 1900-2000 nm, while this power can be emitted in continuous wave mode or by several pulses at pulse durations of a few microseconds to a few seconds.

6. The system according to claim 1 wherein said diode laser device has an average laser power above 40 W at a wavelength in the spectral range of 1400-1500 nm, while this power can be emitted in continuous wave mode or by several pulses at pulse durations of a few microseconds to a few seconds.

7. The A system according to claim 1 wherein said application system has a silica fiber, which is constructed in a way that the laser radiation is not emitted via the distal fiber end face but via a small area of the cladding surface.

8. The system according to claim 1 wherein said application system has a silica fiber equipped with two devices, which limit the possibility of moving said silica fiber forward and backward inside a medical instrument.

9. The system according to claim 1 wherein the cw power $P_{cw}$ and the peak power of a laser pulse $P_{peak}$ can be set independently from each other; especially the ratio $P_{cw}/P_{peak}$ is variably selectable.

10. The system according to claim 1 wherein the pulse duration $t_{pulse}$, the pulse pause $t_{pause}$ as well as the number of laser pulses are variably selectable.

11. The system according to claim 1 wherein the laser radiation has a wavelength within the spectral region from 800 to 1100 nm, where the wavelength is preferably selected from the group 810 nm, 940 nm and 980 nm.

12. The system according to claim 1 wherein the laser radiation has a wavelength within the spectral region from 1400 to 1500 nm, where the wavelength is preferably 1470 nm.

13. The system according to claim 1 wherein said diode laser system comprises at least two laser devices, one that emits light at said first wavelength $\lambda_1$ and a second diode laser device that emits light at said second wavelength $\lambda_2$.

14. A system according to claim 1 for the treatment of BPH, for use in a tumor resection or for use in thoracic surgery.

* * * * *